United States Patent [19]

Marsella

[11] Patent Number: 4,680,393
[45] Date of Patent: Jul. 14, 1987

[54] PROCESS FOR THE SELECTIVE SYNTHESIS OF TERTIARY ALKANOLAMINES

[75] Inventor: John A. Marsella, Allentown, Pa.

[73] Assignee: Air Products and Chamicals, Inc., Allentown, Pa.

[21] Appl. No.: 861,029

[22] Filed: May 8, 1986

[51] Int. Cl.[4] ............... C07C 85/06; C07C 91/06; C07D 295/08
[52] U.S. Cl. ............................ 544/170; 548/574; 564/480; 564/503
[58] Field of Search .............. 544/170; 548/574; 564/480, 503

[56] References Cited

U.S. PATENT DOCUMENTS

| | | | |
|---|---|---|---|
| 3,270,059 | 8/1966 | Winderl et al. | 564/480 |
| 3,708,539 | 1/1973 | Fenton | 564/480 |
| 4,487,967 | 12/1984 | Stogryn et al. | 564/474 |

FOREIGN PATENT DOCUMENTS 034480  2/1981  European Pat. Off. .

OTHER PUBLICATIONS

Grigg, et al, J.C.S. Chem. Comm., pp. 611–612, (1981).
Murahashi, et al., in Tetrahedron Letters, (vol. 23, No. 2, pp. 229–232, (1982).
Arcelli, et al., in the Journal of Organometallic Chemistry, vol. 235, pp. 93–96, (1982).

*Primary Examiner*—Robert W. Ramsuer
*Attorney, Agent, or Firm*—Mark L. Rodgers; E. Eugene Innis; James C. Simmons

[57] ABSTRACT

The present invention is a process for the synthesis of tertiary alkanolamines by reacting a secondary amine with an alkanediol. High selectivity for the production of alkanolamines is achieved by carrying out the reaction in the presence of a compound or complex of ruthenium in chemical combination or in admixture with an organic phosphine ligand. The organic phosphine ligand is present in an amount such that the ratio of gram mole ligand/gram atom ruthenium is greater than 5.

23 Claims, No Drawings

PROCESS FOR THE SELECTIVE SYNTHESIS OF TERTIARY ALKANOLAMINES

TECHNICAL FIELD OF THE INVENTION

The present invention relates to the catalytic synthesis of tertiary alkanolamines from alkanediols and secondary amines.

BACKGROUND OF THE INVENTION

It is known to produce certain N-substituted alkanediamines and various alkanolamines from dichloroalkanes and alkylene oxides, respectively. These starting materials are expensive and/or extremely toxic. The toxic nature of some of the alkylene oxides is a special problem for small-scale users, since the unit costs of installing safeguards and monitoring systems increase with decreasing production scale.

Previous prior art attempts at aminating alkanediols have typically been limited to high temperature reactions utilizing heterogeneous catalysts. The high temperatures required in the prior art methods led to high operating pressures and low selectivities.

A limited number of prior art disclosures describe the use of homogeneous catalysts, e.g. RhH(PPh$_3$)$_4$, for the reaction of monoalcohols with amines. (See, for example, Grigg. et al, *J.C.S. Chem. Comm.*, pp 611-612 [1981]).

European Patent Publication No. 034,480 describes in general the preparation of N-alkylamine or N,N-dialkylamine by reacting a primary or secondary amine with a primary or secondary alcohol in the presence of certain noble metal catalysts, such as a salt or complex of the noble metal. The preferred example of catalyst is a rhodium hydride-triphenylphosphine complex. Although the disclosure is concerned largely with reactions involving monofunctional alcohols, there is also disclosed the reaction of a primary amine with a diol for the formation of heterocyclic ring compounds containing the amine N atom. For this purpose, the diol used should contain at least four atoms in the chain so that cyclization can occur. The publication contains no disclosure of reaction of a diol with secondary amine, wherein cyclization is not possible.

An article by Murahashi. et al. in *Tetrahedron Letters* (vol. 23, No. 2. pp. 229-232, [1982]) describes the synthesis of secondary amines by reaction of alcohols with amines in the presence of RuH$_2$(PPh$_3$)$_4$ catalyst. By the reaction of butane diol or higher alkane diols with n-hexylamine, N-heterocyclic compounds are formed.

U.S. Pat. No. 3,708,539 discloses the condensation of amines with alcohols in the presence of ruthenium or certain other noble metal catalysts introduced as halides. The process is preferably conducted in the presence of a biphilic ligand of the structure ER$_3$, wherein E may be phosphorus or arsenic. Particular examples are directed to (1) reaction of butanol with dibutylamine obtaining tributylamine; (2) using hexanol as reactant in the same manner resulted in the formation of dibutylhexylamine.

U.S. Pat. No. 4,487,967 discloses a process for selectively preparing severely sterically hindered secondary aminoether alcohols by reacting a primary amino compound with a polyalkenyl ether glycol in the presence of a hydrogenation catalyst at elevated temperatures and pressures.

Reaction of diols with ammonia or alkylamines to produce diaminoalkanes is disclosed in U.S. Pat. No. 3,270,059. The reaction is carried out in the presence of hydrogen at 150°-300° C. and at a pressure of at least 10 atmospheres, over solid catalysts which contain at least one metal from the group consisting of cobalt and nickel. When a secondary amine is employed as a reactant, tertiary diamines are obtained. Reaction of ethylene glycol with diethylamine under the conditions of the patent yields chiefly tetraethylethylene diamine and a lesser amount of diethylethanolamine.

The selective conversion of primary aliphatic amines to yield (I) N.N-dimethylalkyl- or (II) N.N-dialkylmethyl-amines by reaction with methanol in the presence of RuCl$_2$(Ph$_3$P)$_3$ catalyst, is disclosed in an article by Arcelli, et al. in the *Journal of Organometallic Chemistry* (vol. 235, pp. 93-96 [1982]). The selectivity towards the I or II type compound is controlled by choice of the amount of catalyst and the ratio of reactants.

SUMMARY OF THE INVENTION

The present invention is a method for improving the selectivity for mono-aminated products in a process for synthesizing alkanolamines by reacting a secondary amine with an alkanediol at a temperature between 125°-200° C. Selectivity for mono-aminated products; i.e alkanolamines vs. alkanediamines, is achieved by carrying out the reaction in the presence of a compound or complex of ruthenium in chemical combination or in admixture with an organic phosphine ligand, such as PPh$_3$. The ligand should be present in an amount such that the ratio of gram mole ligand/gram atom ruthenium is greater than 5.

The use of excess phosphine ligand; i.e., a gram molar amount greater than 5 times the gram atom amount of rutheniums results in high selectivity for the formation of tertiary alkanolamines even at high temperatures; i.e., 125°-200° C. In accordance with this process, both high selectivity and high conversions are achieved.

DETAILED DESCRIPTION OF THE INVENTION

The process of the present invention achieves high selectivity of tertiary alkanolamines by the reaction of an alkanediol with a secondary amine at high temperatures. High alkanolamine selectivity; i.e., mono-amination, is achieved by carrying out the amination process in the presence of a compound or complex of ruthenium in chemical combination or in admixture with an excess amount of an organic phosphine ligand. The organic phosphine ligand should be present in an amount such that the ratio of gram mole ligand/gram atom ruthenium is greater than 5/1 and preferably is greater than 8/1.

Secondary amines which are useful for this reaction can be represented by the formula: HNR$_2$ in which —NR$_2$ is

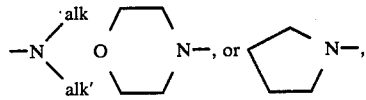

and in which "alk" and "alk'" are alkyl groups of up to 20 carbon atoms.

The alkanediols can include up to 12 carbon atoms with a linear or branched carbon skeleton. Preferably the hydroxyl groups of the alcohol functionalities should be separated by not more than one carbon. Most preferably, the diols should be vicinal diols. Example of most preferred diols include ethylene glycol, 1,2-propanediol, 2,3-butanediol, 3-methyl-1,2-propanediol, 2,3-butanediol, 3-methyl-1,2-butanediol, 1,2-cyclohexanediol and 1,2-cyclododecanediol.

The concentration of the secondary amine may be in the range 0.5 to 10 moles per liter of reaction medium, and is preferably in the range of 1 to 5 mols/liter. The catalyst concentration may be generally in the range of $10^{-4}$ to $10^{-1}$ mols per liter of reaction medium, and preferably $10^{-3}$ to $10^{-2}$ mols/liter.

The catalysts which can be used in the present reaction comprise a ruthenium compound or complex in chemical combination or admixture with an organic phosphine ligand. Examples of phosphine ligands suitable for this reaction include $PPh_3$, $P(p-C_6H_4F)_3$, $P(Ph)Me_2$, $P(p-tol)_3$, $P(C_6F_5)_3$, $P(OPh)_3$, DPPM, $PPh_2Me$, $P(i-Pr)_3$, DPPE, $PPh(C_6F_5)_2$, $P(o-C_6H_4NMe_2)$, $P(o-tol)_3$ and mixtures thereof. Specific examples of ruthenium compounds or complexes which can be combined or admixed with the phosphine ligand to favor tertiary alkanolamine formation include: $RuCl_2(PPh_3)_3$, $RuHCl(PPh_3)_3$, $RuCl_3xH_2O$, $Ru(NH_3)_6Cl_3$, $K_2(RuCl_5)_2O$, $Ru(NO)Cl_3$, $K_2RuCl_5$, $K_2RuCl_6$, $Ru(NH_3)_6 Cl_2$, $K_2RuO_4$, $RuCl_2(DMSO)_4$, "Ruthenium Red" (ammoniated ruthenium oxychloride), anhydrous $RuCl_3$, etc.

The catalysts employed in the practice of the invention, without being bound to any particular theory, apparently function as homogeneous catalysts, since they are at least partially dissolved in the reaction medium. As a result, such catalysts obtain more selective product distribution than that obtained using heterogeneous catalysts.

Moreover, the addition of excess catalyst modifier, i.e., organic phosphine ligand has a marked effect on the behavior of the homogeneous catalyst. High selectivity and high conversion are achieved at temperatures at which prior processes typically obtained both poor selectivity and poor conversion., i.e., 125°–200° C. and preferably between 150°–200° C.

The process is preferably carried out at autogenous pressure without requiring addition of hydrogen to the system, although hydrogen may be employed, if desired. Additionally, by the practice of the present invention, the selective synthesis of alkanolamines is made possible utilizing readily available and relatively low toxicity starting materials.

The exact composition and structure of the active catalyst species promoting the reaction is not clear since the form in which the catalyst is introduced may function merely as a precursor to the active structure formed in the medium under reaction conditions. While carbonyl complexes have been observed in reaction mixtures. the use of isolated neutral carbonyl complexes of ruthenium, as such catalyst precursors, were found to lead to lower catalytic activity.

The process of the invention may be carried out in the presence of added solvents or diluents, among which are preferred; N-methylpyrrolidinone, N,N-dimethylacetamide, dimethylsulfoxide (DMSO), water, 1,2-dimethoxyethane.

The present process typically exhibits higher selectivity toward tertiary alkanolamines at high conversions than prior art processes using heterogeneous transition metal catalysts. such as Example 6 of U.S. Pat. No. 3,270,059. The tertiary alkanolamines produced by the present process are useful as urethane catalysts, acid-gas scrubbers, anti-corrosion agents and in other applications.

Several operating examples of the present process were carried out and are described below. These examples are only meant to illustrate the present invention and are not meant to be limiting.

The product distributions from the operating examples are reported as a selectivity coefficient (r) which is defined as:

$$r = \frac{Yd}{Ym + Yd}$$

where
Ym = yield of mono-aminated product(s)
Yd = yield of diaminated product(s)

A selectivity coefficient (r) of 0.5 indicates a 50/50 mixture (on an equivalent nitrogen basis) of mono- and di- aminated products, with a value of $r>0.5$ indicating more diaminated products and a value $r<0.5$ indicating more mono-aminated product. Processes in which a high selectivity for mono-aminated products is desired should have a selectivity coefficient of no greater than about $r=0.1$ and preferably no greater than $r=0.03$.

EXAMPLE 1

A 22 ml stainless steel Parr bomb reactor was charged with 5.5 g ethylene glycol (88.6 mol), 1.01 g morpholine (11.5 mol), 130 mg $RuCl_3(PPh_3)_3$ ($1.3 \times 10^{-4}$ mol) 250 mg $PPh_3$ ($9.5 \times 10^{-4}$ mol) 0.52 g N-methylpyrrolidinone (as internal standard) and a magnetic stirring bar in a nitrogen-filled glove box. The bomb was sealed and placed in a previously-heated oil bath with stirring. After heating for 2.5 h at 180° C., the reactor pressure was 44 psig. At this point, the bomb was cooled to room temperature at which point the pressure stood at 17 psig. The reactor was vented, opened and the contents analyzed by GLC. The analysis showed that all of the morpholine had reacted to give 1.42 g hydroxyethylmorpholine (93% yield) and 0.04 g bismorpholinoethane (3% yield).

The ratio of gram mole phosphine ligand/gram atom ruthenium was calculated to be about 10.3/1. The selectivity coefficient (r), as defined above, was calculated to be r=0.03, indicating a very high selectivity for monoaminated product, i.e., hydroxyethylmorpholine.

EXAMPLE 2 (COMPARATIVE)

A procedure substantially identical to that in Example 1 was followed for reacting morpholine and ethylene glycol, except that $RuCl_2(PPh_3)_3$ without additional triphenylphosphine was employed as the catalyst. In this case, the maximum pressure achieved was 79 psig and the final pressure on cooling was 29 psig. This run gave 44% yield of hydroxyethylmorpholine and 51% yield of bismorpholinoethane.

The gram mole phosphine ligand/gram atom ruthenium ratio was 3/1, and the selectivity coefficient was calculated to be r=0.54. This example shows that by operating without an excess of $PPh_3$, e.g. substantially under the conditions of Arcelli. et al., *J. Organometal. Chem.* 235 (1982) 93-96. no selectivity favoring monoamination is observed. Additionally. both operating and final pressures were significantly higher in the latter case.

EXAMPLE 3

The procedure and catalyst composition of Example 1 was used to react 0.56 (12.4 mol) dimethylamine with 5.5 g (72 mol) 1,2-propanediol at 180° C. for 2.5 hr. The maximum pressure achieved in this case was 115 psig with the final pressure being 42 psig. These conditions gave 98.5% conversion of the dimethylamine, with the final product selectivities being 54% 1-dimethylamino-2-propanol, 25% 2-dimethylamino-1-propanol, (79% total to mono-amination) and 2% N,N,N -1,2-ethanediamine.

The gram mole phosphine ligand/gram atom ruthenium ratio was 10.3/1, and the selectivity coefficient was calculated to be r=0.02. indicating high selectivity toward mono-amination.

EXAMPLE 4

The procedure of Example 1 was repeated using a catalyst system consisting of 39 mg $RuCl_3 \times H_2O$ (43.1% Ru, $1.7 \times 10^{-4}$ mol Ru) and 226 mg $PPh_3$ ($8.6 \times 10^{-4}$ mol). In this run, the maximum reaction pressure was 71 psig which, on cooling to room temperature. dropped to 27 psig. Analysis of reaction products showed 100% conversion of morpholine with yields of hydroxyethylmorpholine and bismorpholinoethane being 87% and 7%, respectively.

The gram mole phosphine ligand/gram atom ruthenium ratio was slightly greater than 5/1 and the selectivity coefficient was r=0.07.

This run indicates that good selectivity toward mono-amination is observed when the ratio of gram mole ligand/gram atom ruthenium is above 5, but the selectivity is lower when compared to runs using a higher ratio.

Having thus described the present invention, what is now deemed appropriate for Letters Patent is set out in the following appended claims.

What is claimed is:

1. In a process for the preparation of a tertiary alkanolamine by reacting a secondary amine with an alkanediol at a temperature between 150°-200° C., the method for improving the selectivity for monoaminated product which comprises: carrying out said reaction in the presence of a compound or complex of ruthenium in chemical combination or in admixture with an organic phosphine ligand, said ligand being present in an amount such that the ratio of gram mole ligand/gram atom ruthenium is greater than 5.

2. The method in accordance with claim 1 wherein said organic phosphine ligand is $PPh_3$.

3. The method in accordance with claim 1 wherein said organic phosphine ligand is selected from the group consistng of $P(p-C_6H_4F)_3$, $P(Ph)Me_2$, $P(p-tol)_3$ and mixtures thereof.

4. The method in accordance with claim 1 wherein said organic phosphine ligand is present in an amount such that the gram mole ligand/gram atom ruthenium ratio is at least 8.

5. The method in accordance with claim 1 wherein said alkanediol is selected from the group consisting of ethylene glycol, 1, 2 propanediol, 2,3 butanediol, 3-methyl-1,2 butanediol, 1.2 cyclohexanediol, 1,2 cyclododecanediol and mixtures thereof.

6. The method in accordance with claim 1 wherein said ruthenium compound or complexes are selected from the group consisting of $RuCl_2(PPh_3$, $RuHCl(PPh_3)_3$, $RuCl_3 \times H_2O$, $Ru(NH_3)_6Cl_3$, $K_2(RuCl_5)_2O$, $Ru(NO)Cl_3$, $K_2RuCl_5$, $K_2RuCl_6$, $Ru(NH_3)_6Cl_2$, $K_2RuO_4$, $RuCl_2(DMSO)_4$, Ruthenium Red, Anhydrous $RuCl_3$ and mixtures thereof.

7. The method in accordance with claim 1 wherein said reaction is carried out at autogenous pressure without the addition of hydrogen.

8. The method in accordance with claim 1 wherein hydrogen is added to the reaction mixture.

9. The method in accordance with claim 1 wherein said reaction is carried out in the presence of an added solvent.

10. The method in accordance with claim 9 wherein said solvent is selected from the group consisting of N-methylpyrrolidinone, N,N-dimethylacetamide, dimethylsulfoxide, water, 1,2-dimethoxyethane.

11. The method in accordance with claim 1 wherein the concentration of the secondary amine is in the range of 0.5 to 10 moles per liter of reaction medium.

12. The method in accordance with claim 1 wherein the ruthenium/phosphine combination or admixture is present in a concentration in the range of $10^{-4}$ to $10^{-1}$ moles per liter of reaction medium.

13. The method in accordance with claim 1 wherein the yield of tertiary alkanolamine is at least 79%.

14. The method in accordance with claim 1 wherein the conversion of the secondary amine is at least 98.5%.

15. The method in accordance with claim 1 wherein said amination takes place in the liquid phase.

16. The method in accordance with claim 1 wherein said alkanediol is ethylene glycol or 1,2 propanediol.

17. The method in accordance with claim 1 wherein said secondary amine is morpholine or dimethylamine.

18. A process for the synthesis of tertiary alkanolamines which comprises reacting a secondary amine with an alkanediol at a temperature between 150°-200 C. and at autogenous pressure, in the presence of an organic solvent or water and a catalyst composition comprising a compound or complex of ruthenium in chemical combination or in admixture with an organic phosphine ligand such that the gram mole ligand/gram atom ruthenium ratio is greater than 5, said catalyst composition being present in a concentration in the range of $10^{-4}$ to $10^{-1}$ moles per liter of reaction medium.

19. The process in accordance with claim 18 wherein said organic phosphine ligand is $PPh_3$.

20. The process in accordance with claim 18 wherein said organic phosphine ligand is present in an amount such that the gram mole ligand/gram atom ruthenium ratio is at least 8.

21. The process in accordance with claim 18 wherein said catalyst composition is present in a concentration in the range of $10^{-3}$ to $10^{-2}$ moles per liter of reaction medium.

22. The process in accordance with claim 18 wherein the alkanediol is selected from the group consisting of ethylene glycol and 1,2 propanediol.

23. The process in accordance with claim 19 wherein the secondary amine is selected from the group consisting of dimethylamine and morpholine.

* * * * *